United States Patent
Martel

(10) Patent No.: US 12,426,978 B2
(45) Date of Patent: Sep. 30, 2025

(54) STERILE COVERING AND ROTATING JOINT DEVICE

(71) Applicant: STERLAB, Vallauris (FR)

(72) Inventor: Paul Martel, Saint-Raphaël (FR)

(73) Assignee: STERLAB, Vallauris (FR)

( * ) Notice: Subject to any disclaimer, the term of this patent is extended or adjusted under 35 U.S.C. 154(b) by 393 days.

(21) Appl. No.: 18/040,794

(22) PCT Filed: Jul. 26, 2021

(86) PCT No.: PCT/FR2021/051395
§ 371 (c)(1),
(2) Date: Feb. 6, 2023

(87) PCT Pub. No.: WO2022/038321
PCT Pub. Date: Feb. 24, 2022

(65) Prior Publication Data
US 2024/0024058 A1 Jan. 25, 2024

(30) Foreign Application Priority Data
Aug. 17, 2020 (FR) .................................... 2008526

(51) Int. Cl.
A61B 46/10 (2016.01)
A61B 46/00 (2016.01)

(52) U.S. Cl.
CPC .............. *A61B 46/10* (2016.02); *A61B 46/40* (2016.02)

(58) Field of Classification Search
None
See application file for complete search history.

(56) References Cited

U.S. PATENT DOCUMENTS 11,096,754 B2 * 8/2021 Soto .................. A61B 34/30
2010/0292707 A1 * 11/2010 Ortmaier .............. B25J 19/0075
606/130

FOREIGN PATENT DOCUMENTS

| EP | 0437004 A2 | 7/1991 |
| EP | 3338668 A1 | 6/2018 |
| WO | 2022038321 A1 | 2/2022 |

OTHER PUBLICATIONS

Foreign Communication from a Related Counterpart Application, International Search Report dated Dec. 3, 2021, International Application No. PCT/FR2021/051395 filed on Jul. 26, 2021.
Foreign Communication from a Related Counterpart Application, Written Opinion dated Dec. 3, 2021, International Application No. PCT/FR2021/051395 filed on Jul. 26, 2021.

* cited by examiner

*Primary Examiner* — Michael W Kahelin
(74) *Attorney, Agent, or Firm* — Conley Rose, P.C.

(57) ABSTRACT

The present invention relates to a sterile covering device with a rotating joint between two attached members, rotating relative to each other and such that the rotating joint connecting the proximal ends of the two members has a groove between these two members, the proximal end of a first cover is able to cover not only the proximal end of the member that it protects but also at least all or part of the groove of the rotating joint, and the proximal end of a second cover is able to cover the proximal end of the other member that it protects and also a part of the proximal end of the first cover that it encloses at the level of the rotating joint, in the groove that the latter has between the two members.

9 Claims, 1 Drawing Sheet

STERILE COVERING AND ROTATING JOINT DEVICE

CROSS-REFERENCE TO RELATED APPLICATIONS

The present application is a filing under 35 U.S.C. 371 as the National Stage of International Application No. PCT/FR2021/051395, filed Jul. 26, 2021, entitled "STERILE COVERING AND ROTATING JOINT DEVICE," which claims priority to French Application No. FR2008526, filed with the Intellectual Property Office of France on Aug. 17, 2020, both of which are incorporated herein by reference in their entirety for all purposes.

TECHNICAL FIELD OF THE INVENTION

The present invention relates to a new sterile protective covering and rotating joint device used in the medical field and more particularly in hospital and clinic operating rooms.

Indeed in a hospital setting, a certain number of standards in terms of hygiene must be respected in order not to transmit diseases to the operating room. However, certain apparatuses used in a hospital setting are very complicated and difficult to sterilize since they are on the one hand very fragile (often with many electronics) and very expensive and, on the other hand, often very large and require particular disinfection. In addition, in the long term, disinfecting products could greatly damage these apparatuses.

For this reason, single-use sterile protective covers, which are much less expensive than conventional disinfection used for surgical equipment, are the ideal solution for optimal sterility while maintaining the quality of the devices used and preserving their use over the long term. They allow considerable savings in time and expenses, especially when the lack of personnel in a hospital environment is known.

Furthermore, medical robotics, in particular during surgical intervention, are being developed more and more, and implement members, often arms, that can perform movements or rotations along the three axes.

One of the applications of the invention is thus the use, but the invention is of course not limited thereto, with a remote manipulator robot for inserting, into the body of a patient, a sheath or fiber, generally semi-rigid, in a natural or artificial pipe, such as a vein or an artery for cardiac interventions, or the urethra, or an access sheath previously implemented to serve as a guide to subsequently insert, for example, an intervention tool, said fiber or sheath necessarily be able to rotate several times on itself.

TECHNICAL BACKGROUND

Thus, in order to protect such robots and apparatuses intended for operating rooms, a wide variety of protective and draping covers, such as those proposed by companies such as in France CG Medical, EDM Imaging, IMMED, etc. (whose catalogs can be viewed without fees on the Internet), which are suitable for all types and brands of apparatuses.

These sterile protective covers thus make it possible to combat the transmission of pathogens. As indicated above, they are parts of rapid and effective solutions for ensuring sterility of operating rooms even with the use of devices and robots which are complicated and difficult to sterilize: They therefore make it possible to protect these robots and apparatuses and consequently the patients. However, although putting this covering in place does not pose major difficulties for devices that have no specific movement or that comprise only parts that move axially, the same is not true for parts connected to one another by a rotating joint which allows them to rotate relative to each other: Certainly in general, this problem is not insurmountable when the rotations occur at a maximum of +/−180° relative to their initial reference position, since it is then sufficient to leave sufficient excess surface area for the cover at the rotating joint, either by accordion-bending or by increasing the lumen of the cover.

However, the problem of covering becomes critical and impossible to solve with current covers and joints when the rotation is performed over one complete revolution or more, since the deformation of the cover no longer allows the rotating part to be tracked relative to the other.

This covering can also be made with one or more covers bonded or assembled to one another for one and the same device: these covers in at least two parts are rigidly connected with one another by any means (glue, pressure tape, etc.) and for which, for example, one can adapt to a support of small diameter, while the other can enclose a larger-diameter part placed at the end of the support (covers for image intensifier arms are one example). However, these multi-part covering devices do not, as indicated above, make it possible to perform more than one complete rotation of one part relative to the other, and no solution has been proposed to date.

In patent publications and patent applications, the rest relate only to protection devices between parts that are movable relative to each other that are either not for single use (and therefore require them to be sterilized themselves, which one is aiming to avoid) or do not protect all the movable parts and the rotating joint that connect them (and which therefore require that at least the unprotected part is sterilized, which is also desired to be avoided), and which in fact are:

either mechanical and rigidly connected permanently to the apparatus as in patent EP3338668 filed by Ethicon on Dec. 21, 2017 on a "protective cover arrangements for a joint interface between a movable jaw and actuator shaft of a surgical instrument".

or flexible and separating an unprotected sterile part and a non-sterile part protected by a cover, as in patent application EP437004 filed by the German company Effner Gmbh on Nov. 15, 1990, which teaches devices for protecting a surgical instrument, in particular an endoscope, against contamination, comprising a tubular cover which is delimited by an insertion opening and an outlet opening comprising an elastic membrane, the outer edge of which is clamped in a frame which expands the tubular cover to which it is connected and which is provided with a central opening enclosing the sterile part of the instrument, the assembly improving the seal of this outlet opening and therefore the sealed connection between the sterile part of the instrument and its non-sterile part which is covered by the sterile cover.

SUMMARY OF THE INVENTION

The problem posed and solved by the present invention is thus to produce the sterile covering of a rotating joint between two parts of a medical apparatus, which are themselves protected by this covering, linked together by this rotating joint and rotating relative to each other over more than one complete revolution, without the risk of uncovering the rotating joint.

To address this problem, the invention proposes a sterile covering and rotating joint device between two attached members, rotating relative to each other and each covered by at least one protective cover wherein:

the rotating joint connecting the proximal ends of the two members has at least one groove between these two members, and as described below and shown in the attached figures, said groove can be formed by the joint itself or be carried by same, the proximal end of a first cover is able to cover not only the proximal end of the member that it protects but also at least a longitudinal part of the groove of the rotating joint and according to the embodiments the totality of the length of this groove and even a part of the end of the other member, the proximal end of a second cover is able to cover the proximal end of the other member that it protects as well as a part of the proximal end of the first cover that this proximal end of a second cover encloses at the rotating joint in the groove that the latter has between the two members.

The proximal ends of the two covers therefore overlap and both partially or completely cover the rotating joint while being independent of movement relative to each other, which gives total freedom to the rotating joint in order to perform rotations without stress over several turns.

In a preferential embodiment, in order to prevent any shrinkage of the covers which would also be exposed to the non-sterile arms to the environment, the opening of the proximal end of the second cover comprises an adjustable lace, which may also be an elastic, and which is able to ensure the continuous contact between the two covers over a part of their overlapping area and at the rotating joint; the proximal end of the second cover thus provides sealing that is relative yet sufficient to protect the environment against the non-sterility of the members and is able to rotate as many times as desired around the proximal end of the first cover by sliding thereon at the level of the rotating joint, the two members then being able to perform more than one complete revolution relative to each other, while remaining protected by the cover.

According to one embodiment of the invention, the rotating joint has an outer transverse dimension smaller than that of the member having itself a smaller outer transverse dimension relative to the other member, either in the case of a surgical robot arm having longitudinal shapes that are cylindrical in revolution, this dimension is the diameter of the rotating joint which is therefore smaller than that of the smallest diameter of the two arms, which creates a groove between the two members.

According to another possible embodiment of the invention, the rotating joint has its outer transverse dimensions, such as its diameter in the case of a cylindrical shape of revolution, equal to or greater than those of the members or arms and then comprises a groove perpendicular to the axis of rotation thereof.

Regardless of the embodiment of said groove, the proximal ends of the two covers, covering at least the rotating joint, therefore overlap in this groove and are even more held in place when the proximal end of the second cover comprises an adjustable lace, which may also be an elastic, which allows this proximal end to be held in the bottom of the groove, which has the consequence of avoiding any longitudinal sliding of the covers which could otherwise create the risk of the rotating joint coming out of position in the overlap area of the two covers.

Thus, the problem posed previously is solved by the present invention, whose advantages are mentioned above and the solutions provided to prove the benefit, according to specific characteristics, as described in more detail below according to the embodiment presented. The disclosure and the attached figures give example embodiments thereof, but other embodiments are possible within the scope of the present invention.

BRIEF DESCRIPTION OF THE FIGURES

Further features and advantages of the invention will become apparent from the following detailed description, which may be understood with reference to the attached drawings in which.

DESCRIPTION OF THE INVENTION

In the description of the invention and for the understanding of the claims, it will be noted that the invention relates to the assembly and the combination of the sterile covering and the rotating joint between two attached members, rotating relative to each other and covered by the covering, and that the term proximal denotes the parts of the elements located on the side of the rotating joint and the term distal denotes the parts remote therefrom.

The axis XX' of rotation of the rotating members relative to each other is shown as being their common longitudinal axis, but the axes of these members could make an angle between them and the rotating joint that connects them could form an elbow.

It will also be noted that the rotating joint can be either a separate member of the members or arms that it connects or a component of a member or arm, or even be composed of two elements each forming part of a member or arm In the following description, identical, similar or analogous elements will be referred to by the same reference numbers.

Example Embodiments

Figure 3:
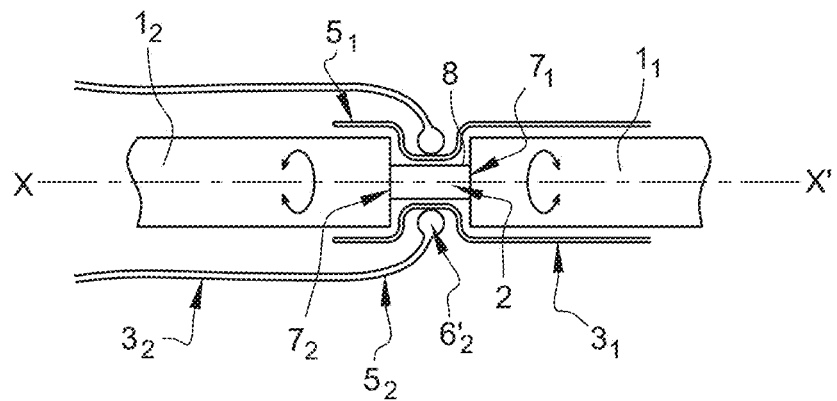
FIG. 3 is a schematic view in longitudinal section of a third example of covering of the same example of a rotating joint according to the invention as in FIG. 2.

Whatever the embodiment, of which three examples are therefore shown in the 3 attached figures, the sterile covering device and a rotating joint 2 between two attached members 1, rotating relative to each other and each covered by at least one protective cover 3 is such that, according to the invention:

the rotating joint 2 connecting the proximal ends 7 of the two members (therefore considered, in the embodiments described below and above, as cylindrical arms of a surgical robot), has at least one groove 8 between the two members 1, the proximal end $5_1$ of a first cover $3_1$ is able to cover not only the proximal end $7_1$ of the member (or arm) $1_1$ that it protects but also at least one longitudinal part of the groove 8 of the rotating joint 2, and even, as shown in the three figures, this proximal end 5$_1$ of this first cover 3$_1$ covers the entirety of the length (along the axis XX') of the groove 8 of the rotating joint 2 and also, as shown in FIG. 3, this proximal end 5$_1$ of this first cover 3$_1$ may also be able to cover a portion of the proximal end 7$_2$ of the other member 1$_2$, the proximal end 5$_2$ of a second cover 3$_2$ is able to cover the proximal end 7$_2$ of the other member (or arm) 1$_2$ that it protects as well as a portion of the proximal end 5$_1$ of the first cover 3$_1$ it encloses into the rotating joint 2 in the groove that the latter has between the two members (or arm) 1.

The two members (arms) 1 being able to perform more than one complete revolution relative to each other, the proximal end 5$_2$ of the second cover 3$_2$ is thus able to turn as many times as desired around the proximal end of the first cover 3$_1$ sliding thereon at the rotating joint 2.

Figure 2:
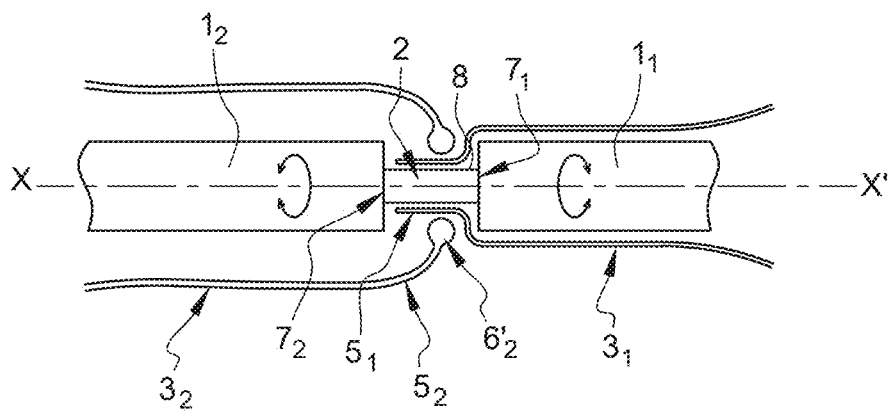
FIG. 2 is a schematic view in longitudinal section of a second example of covering of a second example of a rotating joint according to the invention and connecting two cylindrical arms of revolution such as those of a surgical robot.

In particular embodiments, the rotating joint 2 has at least one external transverse dimension smaller than that of the member 1 itself having a smaller external transverse dimension relative to the other member, in such a way that the rotating joint 2 itself forms said groove 8, at least at this transverse dimension; thus, in the case of a surgical robot arm 1, having longitudinal shapes that are cylindrical in revolution as shown in the examples of FIGS. 2 and 3, where the arms are additionally shown as being of the same diameter, this dimension is the diameter of the rotating joint 8 which is therefore less than that of the smallest diameter of the two arms 1, namely in the case at hand, that of the diameter of the two arms, which creates a groove 8 between the two members (arms) 1.

Figure 1:
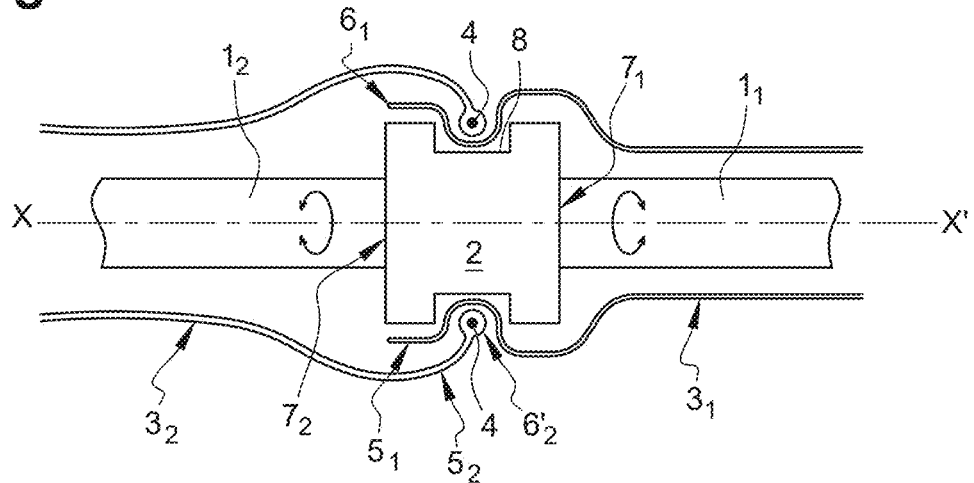
FIG. 1 is a schematic view in longitudinal section of a first example of covering of a first example of a rotating joint according to the invention and connecting two cylindrical arms of revolution such as those of a surgical robot.

According to other embodiments, as shown in FIG. 1, the rotating joint 2 itself comprises a groove 8 perpendicular to the axis of rotation XX' of the latter and the stroke of such a rotating joint 2 can have transverse dimensions (such as in this case, its diameter) greater than those of the two members (arms) 1.

In these example embodiments where the two members 2 are cylindrical arms of axis XX' rotating relative to each other along that axis, the covers 3 are tubular and are able to each be threaded onto one of the arms 2 by the distal end thereof (not shown in the figures).

As previously indicated, in order to prevent any retraction of the covers 3, the opening 6$_2$' of the proximal end 5$_2$ of the second cover 3$_2$ preferably includes an adjustable lace 4 capable of ensuring the permanent contact between the two covers 3 over a part of their overlapping area, or in the groove 8 at the rotating joint 2, and this adjustable lace 4 may be an elastic.

Thus, the first cover 3$_1$, which is therefore preferably tubular, as is generally the case, and which has two openings 6 opposite at its two ends:

is fitted (either from the right to the left of the figures in the exemplary embodiments shown in the figures) via one of its openings (which will be the one called proximal 6$_1$, once in place) onto one of the members 1$_1$, which is considered in the embodiments described as being a first cylindrical arm of a surgical robot, from the distal end (not shown and located beyond the right-hand side of the figures) thereof, covers this first arm 1$_1$ it protects, then all or part of the rotational connecting joint 2 with the other member 1$_2$ that is considered to be the second cylindrical arm of the surgical robot connected to the first arm 1$_1$ by the connecting joint 2, and and optionally covers (as shown in FIG. 3) a portion of the proximal end 7$_2$ of this second arm 1$_2$, then a second cover 3$_2$, tubular and with two openings 6' that are likewise opposite, is also fitted (from the right to the left), via one of its openings (and which will be the distal one once put in place, but not shown and located beyond the left of the figures), from the same distal end of the first arm 1$_1$ as the first cover 3$_1$ and over the latter (because the distal end, not shown, of the second arm 1$_2$ is generally attached on a support which does not allow a cover to be fitted by that end) and is then threaded, passing around the rotating joint 2, on the second arm 1$_2$ to protect it, until the proximal end 5$_2$ of this second cover 3$_2$ positions itself in front of the proximal end 7$_2$ of the second arm 1$_2$, by then partially or totally covering the rotating joint 2 that the opening 6$_2$' of this second cover 3$_2$ encloses by any means such as an adjustable lace 4, and which may be elastic.

The invention claimed is:

1. A sterile covering and rotating joint device between two attached members, rotating relative to each other and each covered by at least one protective cover able to cover the proximal end of the member that it protects, and comprising at least one groove, wherein:
   the at least one groove is between the two members and is on the rotating joint connecting the proximal ends of the two members,
   the proximal end of a first cover, which is able to cover the proximal end of the member that it protects, is also able to cover at least one longitudinal part of the groove of the rotating joint,
   the proximal end of a second cover, which is able to cover the proximal end of the other member that it protects, is able to also cover a portion of the proximal end of the first cover that this proximal end of a second cover encloses at the rotating joint in the groove with the rotating joint between the two members.

2. The device according to claim 1, wherein the two members are able to perform more than one complete revolution relative to each other, the proximal end of the second cover is thus able to turn as many times as desired around the proximal end of the first cover sliding thereon at the rotating joint.

3. The device according to claim 1, wherein the proximal end of the first cover is able to cover at least the entire length of the groove of the rotating joint.

4. The device according to claim 3, wherein the proximal end of the first cover is able to cover a portion of the proximal end of the other member.

5. The device according to claim 1, wherein the rotating joint connecting the proximal ends of the two members has at least one outer transverse dimension smaller than the one of the member which has itself a smaller outer transverse dimension relative to the other members, in such a way that the rotating joint itself forms said groove, at least in this transverse dimension.

6. The device according to claim 1, wherein the rotating joint includes a groove perpendicular to the axis of rotation thereof.

7. The device according to claim 1, wherein the two members are cylindrical arms of axis XX' rotating relative to each other along this axis, wherein the covers are tubular and are able each to be threaded on one of the arms by the distal end thereof.

8. The device according to claim 1, wherein an opening from the proximal end of the second cover includes an adjustable lace capable of ensuring permanent contact between the two covers over a part of their overlapping area in the groove.

9. The device according to claim 8, wherein the adjustable lace is an elastic.

\* \* \* \* \*